(12) United States Patent
Hamuro (10) Patent No.: US 10,485,947 B2
(45) Date of Patent: Nov. 26, 2019

(54) METHOD FOR MANUFACTURING MEDICAL LONG BODY

(71) Applicant: TERUMO KABUSHIKI KAISHA, Shibuya-ku, Tokyo (JP)

(72) Inventor: Kouta Hamuro, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 95 days.

(21) Appl. No.: 15/416,455

(22) Filed: Jan. 26, 2017

(65) Prior Publication Data

US 2017/0136208 A1    May 18, 2017

Related U.S. Application Data

(63) Continuation of application No. PCT/JP2015/076099, filed on Sep. 15, 2015.

(30) Foreign Application Priority Data

Sep. 29, 2014   (JP) .................. 2014-198271

(51) Int. Cl.
*A61M 25/00* (2006.01)
*B29C 70/68* (2006.01)
(Continued)

(52) U.S. Cl.
CPC .... *A61M 25/0009* (2013.01); *A61M 25/0012* (2013.01); *B29C 35/16* (2013.01);
(Continued)

(58) Field of Classification Search
CPC .................. A61M 25/0012; A61M 25/009
See application file for complete search history.

(56) References Cited

U.S. PATENT DOCUMENTS

| 6,077,258 A | 6/2000 | Lange et al. |
| 2001/0018933 A1 | 9/2001 | Martucci et al. |
| 2013/0079746 A1 | 3/2013 | Fischell et al. |

FOREIGN PATENT DOCUMENTS

| JP | 2000-220771 A | 8/2000 |
| JP | 2001-299923 A | 10/2001 |
| JP | 2001-327605 A | 11/2001 |

OTHER PUBLICATIONS

Machine translation of JP 2001-327605 A, Dec. 4, 2018 (Year: 2018).*

(Continued)

*Primary Examiner* — Benjamin A Schiffman
(74) *Attorney, Agent, or Firm* — Buchanan Ingersoll & Rooney PC (57) ABSTRACT

A method of manufacturing a medical elongated body including an inner layer, an outer layer covering the outside of the inner layer, and a reinforcement body provided between the inner layer and the outer layer. The method includes an inner layer forming step of forming the inner layer, a reinforcement body forming step of forming the reinforcement body on an outer peripheral surface of the inner layer after the inner layer forming step, a cooling step of cooling at least a predetermined spot of the inner layer after the reinforcement body forming step, and an annealing step of annealing the reinforcement body which overlaps the predetermined spot of the inner layer cooled by the cooling step.

15 Claims, 9 Drawing Sheets

(51) Int. Cl.
  B29C 35/16  (2006.01)
  B29C 71/02  (2006.01)
  B29C 41/22  (2006.01)
  B29C 70/72  (2006.01)
  B29C 48/00  (2019.01)
  *A61L 29/04*   (2006.01)
  *B29K 77/00*   (2006.01)
  *B29L 9/00*    (2006.01)
  *B29L 31/00*   (2006.01)
  *B29C 48/09*   (2019.01)
  *B29C 48/21*   (2019.01)

(52) U.S. Cl.
  CPC .............. *B29C 41/22* (2013.01); *B29C 48/00* (2019.02); *B29C 70/687* (2013.01); *B29C 70/688* (2013.01); *B29C 70/72* (2013.01); *B29C 71/02* (2013.01); *A61L 29/04* (2013.01); *B29C 48/0022* (2019.02); *B29C 48/09* (2019.02); *B29C 48/21* (2019.02); *B29C 2035/165* (2013.01); *B29C 2071/022* (2013.01); *B29C 2793/0027* (2013.01); *B29K 2077/00* (2013.01); *B29K 2995/0013* (2013.01); *B29L 2009/00* (2013.01); *B29L 2031/7542* (2013.01)

(56) References Cited

OTHER PUBLICATIONS

Machine translation of JP 2001-299923 A, Dec. 4, 2018 (Year: 2018).*
International Search Report (PCT/ISA/210) dated Dec. 1, 2015, by the Japanese Patent Office as the International Searching Authority for International Application No. PCT/JP2015/076099.
Written Opinion (PCT/ISA/237) dated Dec. 1, 2015, by the Japanese Patent Office as the International Searching Authority for International Application No. PCT/JP2015/076099.

* cited by examiner

METHOD FOR MANUFACTURING MEDICAL LONG BODY

CROSS-REFERENCE TO RELATED APPLICATIONS

This application is a continuation of International Application No. PCT/JP2015/076099 filed on Sep. 15, 2015, which claims priority to Japanese Application Number 2014-198271 filed on Sep. 29, 2014, the entire contents of both which are incorporated herein by reference.

TECHNICAL FIELD

The disclosure herein relates to a method of manufacturing a medical elongated body in which a reinforcement body is provided between an inner layer and an outer layer.

BACKGROUND ART

In order to obtain desired delivery performance, a medical elongated body such as a catheter is structured to include an inner layer, an outer layer covering the outside of the inner layer, and a reinforcement body that is provided between the inner layer and the outer layer. This type of medical elongated body is manufactured by forming the inner layer, the reinforcement body, and the outer layer sequentially from an axial center to the outside in a radial direction, and suitably performing processes (cutting, shaping, attachment of configuration components, and the like) in the middle of the formation. The reinforcement body is generally formed of reinforcement wires which are metallic wires.

For example, JP-A-2008-167826 discloses a manufacturing method of cutting a stacked cylindrical body in which an inner layer and a reinforcement body are formed, attaching a ring-shaped contrast marker thereto, and thereafter, coating the stacked cylindrical body with an outer layer. According to this manufacturing method, it is possible to prevent the coming apart of multiple reinforcement wires of the reinforcement body by melting and integrating the inner layer and the reinforcement body together via heating of the reinforcement body when cutting the stacked cylindrical body.

As means for preventing the coming apart of the reinforcement wires when the reinforcement body is cut, there is a method of annealing (annealing process) the reinforcement body in addition to the method disclosed in JP-A-2008-167826. Since it is possible to eliminate stress of the reinforcement wires of the reinforcement body according to this method, it is possible to prevent the jumping of the reinforcement wires even if the reinforcement body is cut. For this reason, the inner layer and the reinforcement body can be well coated with the outer layer.

In a case where an annealing process is performed on a medical elongated body, since heat is transferred to an inner layer from a reinforcement body, unintended spots of the inner layer may melt or burn. In some cases, a defect occurs, for example, a portion of the inner layer of the medical elongated body gets a hole, and the reinforcement body is exposed. Particularly, the inner layer of the medical elongated body is desirably made of thermoplastic resin which can be easily molded into a desired shape and be manufactured at low cost. In contrast, since this type of material has a low melting point, the material may melt simply due to the annealing process.

The disclosure here is made to solve that problem, and to provide a method of manufacturing a medical elongated body by which it is possible to simply prevent the melting of an inner layer even if a reinforcement body is heated, and thus, it is possible to manufacture medical elongated bodies at a high yield.

SUMMARY

According to an aspect of the disclosure herein, there is provided a method of manufacturing a medical elongated body including an inner layer, an outer layer covering the outside of the inner layer, and a reinforcement body provided between the inner layer and the outer layer, the method including: an inner layer forming step of forming the inner layer; a reinforcement body forming step of forming the reinforcement body on an outer peripheral surface of the inner layer after the inner layer forming step; a cooling step of cooling at least a predetermined spot of the inner layer after the reinforcement body forming step; and an annealing step of annealing the reinforcement body which overlaps the predetermined spot of the inner layer cooled by the cooling step.

In the aforementioned description, according to the method of manufacturing the medical elongated body, when the annealing step is performed, it is possible to prevent the melting of the inner layer by performing the cooling step of cooling the predetermined spot of the inner layer. That is, even if heat applied to the reinforcement body is transferred to the inner layer during the annealing step, it is possible to decrease the temperature of the inner layer by performing the cooling step, and thus it is possible to prevent the temperature of the inner layer from increasing to a melting point. As a result, it is possible to maintain the molding state of the inner layer of the medical elongated body well, and to manufacture the medical elongated body at a high yield.

In this case, the inner layer may be formed of thermoplastic resin.

According to the disclosure, since the temperature of the inner layer is decreased by performing the cooling step, during the annealing step, it is possible to prevent the melting of the inner layer which is caused by heat of the annealing step. For this reason, the inner layer of the medical elongated body may be formed of thermoplastic resin, the molding of which can be easily performed at low cost. Since it is possible to prevent the melting of thermoplastic resin having a low melting point by performing the cooling step, it is possible to smoothly process the annealing step and processes following the annealing step, and to manufacture the medical elongated body with high accuracy.

In the cooling step, the predetermined spot is preferably cooled by a coolant having a temperature of $-10°$ C. or lower.

Since the inner layer is cooled by a coolant having a temperature of $-10°$ C. or lower in the cooling step, even if high heat is applied to the inner layer during the annealing step, it is possible to more reliably prevent the melting of the inner layer.

In the cooling step, the predetermined spot may be cooled by dipping the predetermined spot in liquid nitrogen before performing the annealing step.

It is possible to considerably shorten the length of time required to perform the cooling step by dipping the predetermined spot of the inner layer into liquid nitrogen and cooling the predetermined spot, and there is no considerable extension in the length of time to manufacture the medical elongated body.

Preferably, the inner layer is formed of resin having a thermal conductivity in a range of 0.05 $W \cdot m^{-1} \cdot K^{-1}$ to 1

W·m$^{-1}$·K$^{-1}$, and the reinforcement body is formed of a reinforcement wire having a thermal conductivity in a range of 5 W·m$^{-1}$·K$^{-1}$ to 500 W·m$^{-1}$K$^{-1}$.

Since the thermal conductivity of the inner layer is in a range of 0.05 W m$^{-1}$·K$^{-1}$ to 1 W·m$^{-1}$·K$^{-1}$, and the thermal conductivity of the reinforcement body is in a range of 5 W·m$^{-1}$·K$^{-1}$ to 500 W·m$^{-1}$·K$^{-1}$, even if the reinforcement body is heated during the annealing step, it is possible to avoid a large amount of heat being transferred to the inner layer. As a result, it is possible to satisfactorily anneal only the reinforcement body.

According to the disclosure, in the manufacturing of the medical elongated body, even if the reinforcement body is heated, it is possible to simply prevent the melting of the inner layer, and thus, it is possible to manufacture the medical elongated bodies at a high yield.

DETAILED DESCRIPTION

Hereinafter, preferred exemplary embodiments (first and second exemplary embodiments) of a method of manufacturing a medical elongated body of the disclosure herein will be described in detail with reference to the accompanying drawings.

Figure 1:
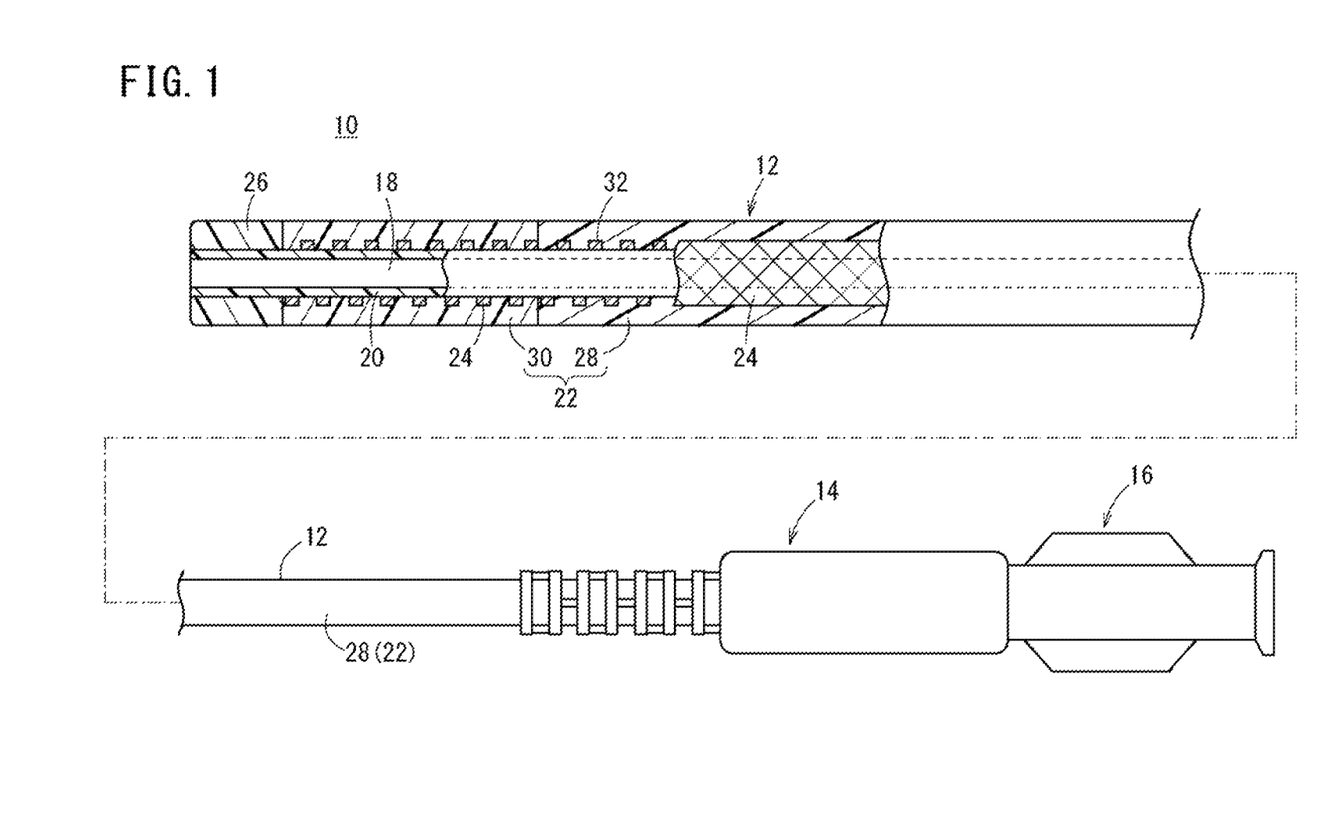
FIG. 1 is a partial side sectional view illustrating a catheter manufactured by a method of manufacturing a catheter according to an exemplary embodiment of the disclosure.

In the first and second exemplary embodiments, a method of manufacturing a guiding catheter which is a medical elongated body 10 illustrated in FIG. 1 will be described in detail. Naturally, the medical elongated body 10 to be manufactured is not limited to a guiding catheter. The disclosure herein can be used in manufacturing a microcatheter, an imaging catheter, an ultrasound catheter, a balloon catheter, an atherectomy catheter, an endoscopic catheter, a catheter for delivering an indwelling object such as a stent, a drug solution delivery catheter, an embolization catheter, a sheath (for example, a guiding sheath) including a reinforcement metallic body, or the like. Alternatively, this manufacturing method can be used in manufacturing various medical devices which are inserted into biological lumens (a blood vessel, a biliary duct, a trachea, an esophagus, a urethra, a nasal cavity, other organs, and the like) in addition to catheters.

Hereinafter, for ease of understanding of the disclosure, the configuration of a guiding catheter 10 (hereinafter, simply referred to as a catheter 10) will be described with reference to FIG. 1. The catheter 10 is configured such that a tube shaped main body 12, a protector 14, and a hub 16 are assembled together.

The tube shaped main body 12 forms a main body portion of the catheter 10 that is inserted into a biological lumen of a patient from the outside. A lumen 18 is formed in such a way as to pass through an axial central portion of the tube shaped main body 12 from a distal end to a proximal end of the tube shaped main body 12 such that another medical device can be inserted into and guided by the lumen 18. It is also possible that multiple lumens 18 may be provided in the tube shaped main body 12. In FIG. 1, the tube shaped main body 12 is illustrated as being straight, and alternatively, a distal side of the tube shaped main body 12 may be shaped in such a way as to be curved or bent.

For example, the outer diameter of the tube shaped main body 12 may be set to a range of 0.5 mm to 6 mm (2 Fr to 18 Fr) such that the tube shaped main body 12 can be inserted into a biological lumen. The axial length of the tube shaped main body 12 differs according to a treatment site or a treatment method, and for example, may be set to a range of 10 cm to 200 cm.

The tube shaped main body 12 preferably has suitable physical properties (flexibility, rigidity, elasticity, the coefficient of friction, kink resistance, drug solution resistance, biocompatibility, and the like) to cope with a biological lumen that is complicatedly curved and bent inside a body. For this reason, the tube shaped main body 12 has a multi-layer structure in which an inner layer 20, an outer layer 22 covering the outside of the inner layer 20, and a reinforcement body 24 provided between the inner layer 20 and the outer layer 22 are stacked on top of each other. A distal portion of the tube shaped main body 12 is provided with a soft tip portion 26 that is made of flexible resin and covers the periphery of the inner layer 20.

The inner layer 20 forms an inner wall of the lumen 18 at a position close to the axial center of the tube shaped main body 12. Preferably, a guide wire or another medical device (both are not illustrated) can be easily slid against the inner layer 20, and the inner layer 20 is harder than the outer layer 22. An inner wall of the inner layer 20 may be coated with a lubricant so as to improve the travelling performance of a guide wire or another medical device.

The inner layer 20 is not limited to a specific material, and thermoplastic resin which can be easily molded by heating may be used as the material of the inner layer 20. Examples of thermoplastic resin includes polymeric materials such as polyolefins (for example, polyethylene, polypropylene, polybutene, an ethylene-propylene copolymer, an ethylene-vinyl acetate copolymer, an ionomer, or a compound of two or more thereof), polystyrene, polyvinyl chloride, polyamide, a polyamide elastomer, polyester, a polyester elastomer, polyurethane, a polyurethane elastomer, polyimide, and fluorine resin, and compounds of the polymeric materials. Polyamide (nylon) among these materials is preferably used since the polyamide has a low coefficient of friction, is tough, and has good wear resistance and good drug solution resistance, and the molding of the polyamide into a tubular shape can be easily performed at low cost. Hereinafter, the catheter 10 including the inner layer 20 formed of polyamide will be described.

The inner layer 20 preferably has a thermal conductivity much lower than that of the reinforcement body 24. For example, the thermal conductivity of the inner layer 20 may be set to a range of 0.05 $W \cdot m^{-1} \cdot K^{-1}$ to 1 $W \cdot m^{-1} \cdot K^{-1}$, and more preferably, may be set to a range of 0.1 $W \cdot m^{-1} \cdot K^{-1}$ to 0.5 $W \cdot m^{-1} \cdot K^{-1}$.

In contrast, the outer layer 22 covers the outside of the inner layer 20 and the reinforcement body 24 such that the outer layer 22 forms a front surface (exterior) of the tube shaped main body 12. For this reason, the outer layer 22 is preferably formed so as to be easily slid inside a biological lumen and so as not to cause damage to the biological lumen. For example, the outer layer 22 may be made of a material softer than that of the inner layer 20. An outer peripheral surface of the outer layer 22 may be coated with a lubricant so as to improve the travelling performance of the catheter 10.

The outer layer 22 includes a main extension portion 28 forming the majority of the tube shaped main body 12, and a distal extension portion 30 that extends a short distance from a distal side of the main extension portion 28 up to the soft tip portion 26. For example, the main extension portion 28 and the distal extension portion 30 are respectively formed of resins having different flexibility, and are formed to have substantially the same outer diameter such that the main extension portion 28 is flush with the distal extension portion 30. The distal extension portion 30 is more flexible than the main extension portion 28, and is harder than the soft tip portion 26. As a result, the flexibility of the tube shaped main body 12 increases in a stepwise manner toward a distal direction, and the travelling performance of the tube shaped main body 12 inside a biological lumen is further improved.

The outer layer 22 is not limited to a specific material, and similar to the inner layer, thermoplastic resin which can be easily molded by heating may be used as the material of the outer layer 22. Examples of thermoplastic resin include polymeric materials such as polyolefins (for example, polyethylene, polypropylene, polybutene, an ethylene-propylene copolymer, an ethylene-vinyl acetate copolymer, an ionomer, or a compound of two or more thereof), polystyrene, polyvinyl chloride, polyamide, a polyamide elastomer, polyester, a polyester elastomer, polyurethane, a polyurethane elastomer, and polyimide, and compounds of the polymeric materials.

The reinforcement body 24 of the tube shaped main body 12 improves the delivery performance of the catheter 10 inside a biological lumen by mainly increasing the rigidity or elastic force of the catheter 10. The reinforcement body 24 is formed by braiding a reinforcement wire 32, which is made of metal or resin, in a mesh-like pattern on an outer peripheral surface of the inner layer 20. Particularly, the reinforcement wire 32 is preferably made of metal such that the reinforcement body 24 can easily maintain a shape and can be easily manufactured.

Examples of the metal of the reinforcement wire 32 include pseudoelastic alloys (including a superelastic alloy) such as a Ni—Ti alloy, a shape-memory alloy, stainless steels (all types of SUSs such as SUS304, SUS303, SUS316, SUS316L, SUS316J1, SUS316J1L, SUS405, SUS430, SUS434, SUS444, SUS429, SUS430F, SUS302), a cobalt alloy, noble metals such as gold and platinum, a tungsten alloy, carbon-based materials (including a piano wire). The reinforcement wire 32 is preferably made of sufficiently thin wires having a circular section, a polygonal section, a flat section, or the like. As a result, it is possible to easily braid the reinforcement wire 32.

The thermal conductivity of the reinforcement body 24 formed by braiding the reinforcement wire 32 differs according to the aforementioned materials. The thermal conductivity may be set to a range of 5 $W \cdot m^{-1} \cdot K^{-1}$ to 500 $W \cdot m^{-1} \cdot K^{-1}$, and more preferably, may be set to a range of 10 $W \cdot m^{-1} \cdot K^{-1}$ to 100 $W \cdot m^{-1} \cdot K^{-1}$.

The arrangement pattern of the reinforcement wire 32 with respect to the inner layer 20 is not limited to a mesh-like pattern and may be various patterns. For example, the reinforcement body 24 may be formed by winding the reinforcement wire 32 into a coil shape along the outer peripheral surface of the inner layer 20.

The soft tip portion (distal flexible portion) 26 provided on the distal side of the tube shaped main body 12 is formed of resin having a flexibility higher than the flexibility of the outer layer 22 and the inner layer 20. The soft tip portion 26 prevents the catheter 10 from causing damage to the inside of a biological lumen when the catheter 10 is being delivered, and improves the travelling performance of the catheter 10.

The soft tip portion 26 is not limited to a specific material. Examples of the material of the soft tip portion 26 include various thermoplastic elastomers such as a styrene elastomer, a polyolefin elastomer, a polyurethane elastomer, a polyester elastomer, a polyamide elastomer, a polybutadiene elastomer, a trans-polyisoprene elastomer, a fluororubber elastomer, and a chlorinated polyethylene elastomer. Particularly, preferably, the material of the soft tip portion 26 is suitably selected according to the material of the inner layer 20. For example, in a case where the inner layer 20 is formed of a material containing polyamide, a polyurethane elastomer may be used as the material of the soft tip portion 26. The soft tip portion 26 may be coated or impregnated with a contrast agent having radiopacity.

The protector 14 of the catheter 10 is attached so as to prevent the kinking of a proximal side of the tube shaped main body 12. The protector 14 covers a distal portion of the hub 16 and is fixed while surrounding and supporting an outer peripheral surface of a proximal portion side of the tube shaped main body 12. As a result, when an operator operates the hub 16, the protector 14 reduces the magnitude of operating force that is locally applied from the hub 16 to a specific spot on the proximal side of the tube shaped main body 12.

The hub 16 of the catheter 10 forms a grip portion that is gripped and operated by an operator during manipulation. In order for the operator to be able to easily grip the hub 16 during manipulation, the hub 16 is formed to have a diameter larger than and a rigidity higher than those of the tube shaped main body 12. The tube shaped main body 12 is rigidly and firmly fixed to a wall portion of the hub 16 which forms an inner space.

Hereinafter, a method of manufacturing the catheter 10 will be described with reference to FIGS. 2 to 5D. In the manufacturing of the catheter 10, basically, the inner layer 20, the reinforcement body 24, and the outer layer 22 are formed sequentially from an axial central portion side to the outside of the tube shaped main body 12.

Figure 2:
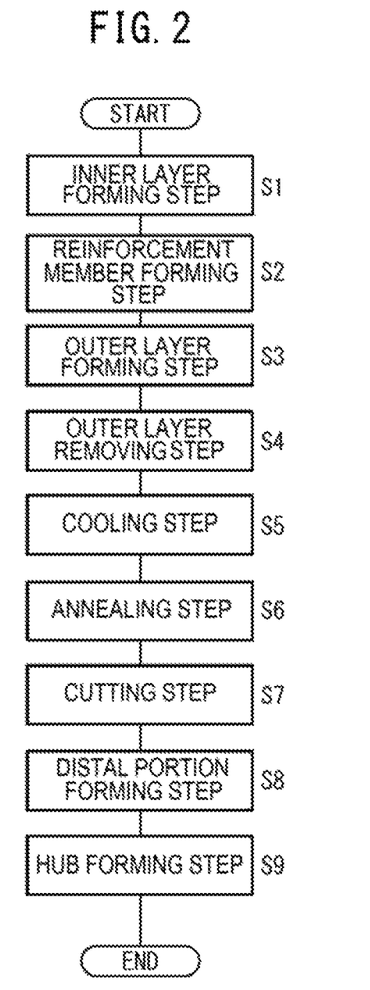
FIG. 2 is a flowchart illustrating steps of manufacturing a catheter of a first exemplary embodiment.
Figure 3A:
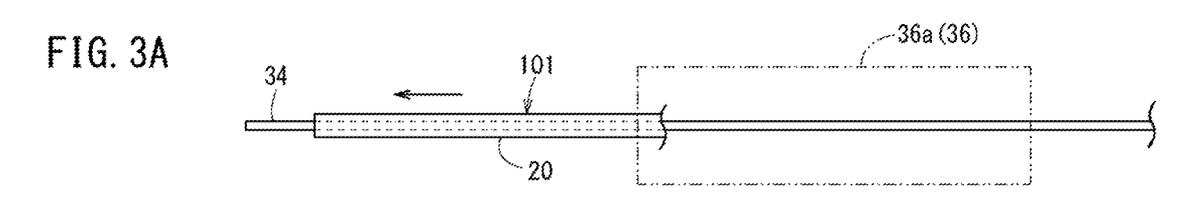
FIG. 3A is a first view illustrating the method of manufacturing a catheter of the first exemplary embodiment.

That is, in the manufacturing of the catheter 10, first, an inner layer forming step is performed (refer to Step S1 in FIG. 2). In the inner layer forming step, the inner layer 20 can be formed via a coating molding method. For example, according to the coating molding method, a core (copper wire or the like) 34 is continuously drawn from rollers (not illustrated), and as illustrated in FIG. 3A, the core 34 is inserted into dies 36a of a precision extrusion molding machine 36, and is moved relative to the dies 36a. Note that the outer diameter (core diameter) of the core 34 is set to be the same as the inner diameter of the lumen 18.

The precision extrusion molding machine 36 extrudes resin (polyamide) melted in a cavity inside the dies 36a, and coats an outer peripheral surface of the core 34 with polyamide. As a result, a first molded object 101, in which the core 34 is coated with polyamide, is continuously discharged from the dies 36a. Polyamide discharged from the dies 36a is molded into the inner layer 20, the outer diameter of which is set by the dies 36a, the inner diameter of which is set by the core 34, and the diameters of which are uniform in an axial direction.

A dip method may be adopted as another molding method of the inner layer forming step. In this case, it is possible to mold the inner layer 20 by melting resin with a solvent in order for the resin to have a suitable viscosity, putting the molten resin in a container, dipping the core 34 into the resin inside the container, coating the periphery of the core 34 with the resin, and then heating the core 34 in a heating furnace set to a curing temperature or higher for a predetermined length of time.

Figure 3B:
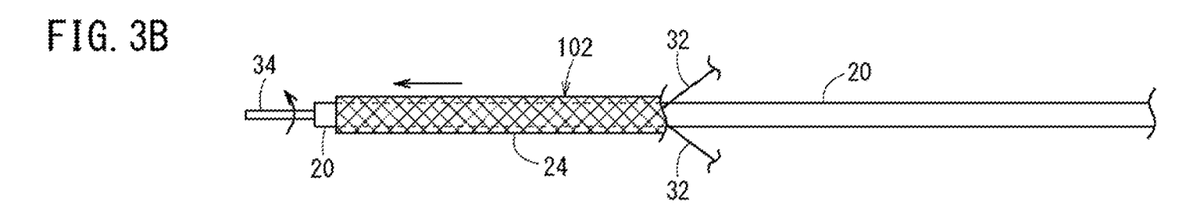
FIG. 3B is a second view illustrating the method of manufacturing a catheter following FIG. 3A.

Subsequently, a reinforcement body forming step is performed on the first molded object 101 (refer to Step S2 in FIG. 2). In the reinforcement body forming step, as illustrated in FIG. 3B, a dedicated winding machine (not illustrated) winds the reinforcement wire 32 around the outside of the inner layer 20 that covers the periphery of the core 34.

For example, the winding machine continuously discharges the reinforcement wire 32 wound around a bobbin (not illustrated) by controlling the bobbin in an associated manner while rotating the first molded object 101. As the first molded object 101 is displaced along the axial direction, the reinforcement wire 32 is wound around the inner layer 20 while being shifted in the axial direction. The wound states (the direction of winding, a pitch between adjacent coating wires, and the like) of the reinforcement wire 32 may be set based on the design of physical properties of the tube shaped main body 12. A second molded object 102 is formed by performing the reinforcement body forming step, and includes the inner layer 20 on the core 34 and the reinforcement body 24 formed of the reinforcement wire 32.

Figure 3C:
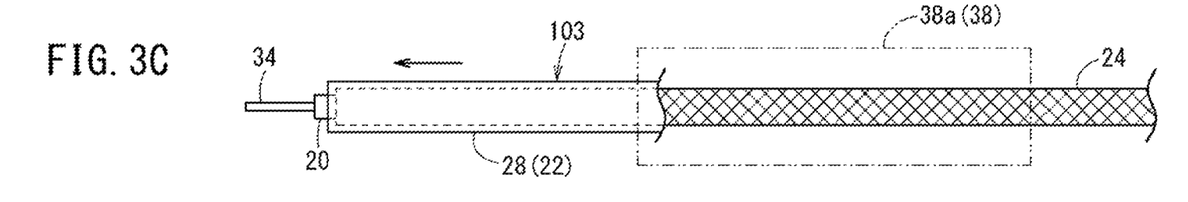
FIG. 3C is a third view illustrating the method of manufacturing a catheter following FIG. 3B.

Subsequently, an outer layer forming step is performed on the second molded object 102 (refer to Step S3 in FIG. 2). Similar to the inner layer forming step, in the outer layer forming step, it is possible to form the outer layer 22 via the coating molding method. That is, the outer layer 22 is continuously molded by inserting the second molded object 102 into dies 38a of a precision extrusion molding machine 38, and extruding resin while moving the second molded object 102 relative to the dies 38a.

Particularly, in the outer layer forming step, the reinforcement wire 32 braided on the outside of the inner layer 20 is coated with the resin of the main extension portion 28 of the outer layer 22 such that the entire reinforcement wire 32 is covered. Resin exposed from the dies 38a is molded into the main extension portion 28, the outer diameter of which is set by the dies 38a, and the diameter of which is uniform in the axial direction. The inner layer 20, the reinforcement body 24, and the main extension portion 28 (the outer layer 22) are stacked on the outside of the core 34 in the radial direction by performing the outer layer forming step. A third molded object 103 is formed by collectively cutting proximal sides (not illustrated) of the core 34, the inner layer 20, the reinforcement body 24, and the outer layer 22 after the outer layer formation step, and has the entire length somewhat longer than the entire length of the tube shaped main body 12 to be molded.

Figure 3D:
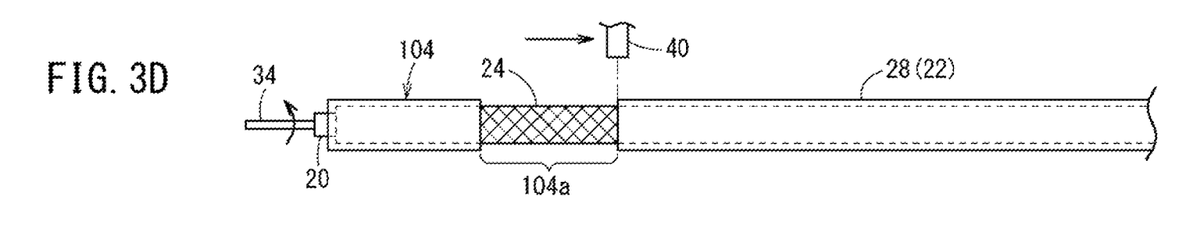
FIG. 3D is a fourth view illustrating the method of manufacturing a catheter following FIG. 3C.

Subsequently, an outer layer removing step is performed on the third molded object 103 (Step S4 in FIG. 2). In the outer layer removing step, a portion of the main extension portion 28, which is close to a distal end thereof and forms the outside of the third molded object 103, is removed. This step is performed so as to form an end portion (distal portion) of the tube shaped main body 12 to be molded.

For example, in the outer layer removing step, it is possible to adopt a laser removal method in which a predetermined range of the main extension portion 28 is evaporated by a laser device 40. In this case, the main extension portion 28 is removed by rotating the third molded object 103 around the axial center thereof while slowly moving the laser device 40, which irradiates laser beams, along the axial direction. As a result, a fourth molded object 104 is molded in which an exposed portion (hereinafter, referred to as an end portion-forming portion 104a) of the reinforcement body 24 is formed in a predetermined range of the third molded object 103 in the axial direction. Particularly, the laser device 40 is capable of emitting laser beams corresponding to only the removed thickness of the main extension portion 28, and is capable of efficiently forming the end portion-forming portion 104a with high accuracy.

A method of removing the main extension portion 28 is not limited to the aforementioned laser removal method and various methods can be adopted. The main extension portion 28 may be removed by dipping a distal portion of the third molded object 103 in a solution that is capable of dissolving only the main extension portion 28.

Subsequently, a cooling step is performed on the fourth molded object 104 (refer to Step S5 in FIG. 2). In the cooling step, the end portion-forming portion 104a of the fourth molded object 104 is cooled so as to prevent the inner layer 20 from dissolving in the following annealing step (Step S8 in FIG. 2).

Figure 4:
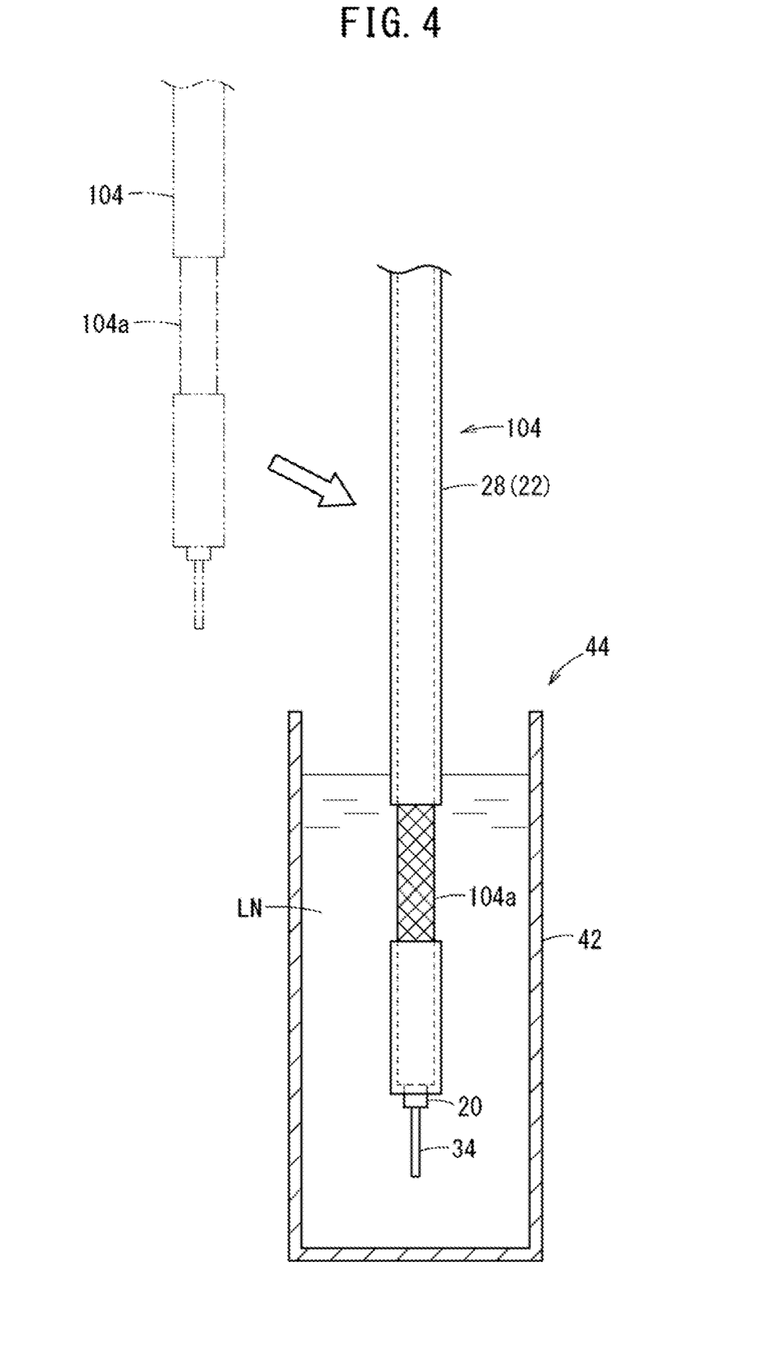
FIG. 4 is a fifth view illustrating the method of manufacturing a catheter following FIG. 3D.

For example, as illustrated in FIG. 4, the cooling step uses a cooling system 44 including a reservoir 42 which has a sufficient depth and in which liquid nitrogen LN is reserved, and a support mechanism (not illustrated) that upward and downward movably supports the fourth molded object 104 via an upper end opening of the reservoir 42. The height of the liquid nitrogen LN reserved in the reservoir 42 is set to a height at which a range from a distal end of the fourth molded object 104 to a proximal end of the end portion-forming portion 104a can be dipped into the liquid nitrogen LN. Note that the reservoir 42 may be formed such that multiple fourth molded objects 104 can be inserted into the reservoir 42 at a time.

The cooling system 44 moves the fourth molded object 104 downward via the support mechanism supporting the fourth molded object 104, inserts the fourth molded object 104 into the liquid nitrogen LN of the reservoir 42 from a distal side of the fourth molded object 104, and dips the end portion-forming portion 104a into the liquid nitrogen LN. Since the temperature of the liquid nitrogen LN is extremely low (−196° C. or lower), the fourth molded object 104 may be moved upward, and the cooling step may be finished immediately after the fourth molded object 104 is moved downward by the support mechanism, and the end portion-forming portion 104a is dipped into the liquid nitrogen LN. The temperatures of the inner layer 20 and the reinforcement body 24 of the end portion-forming portion 104a are considerably decreased from the ambient temperature by the liquid nitrogen LN.

Figure 5A:
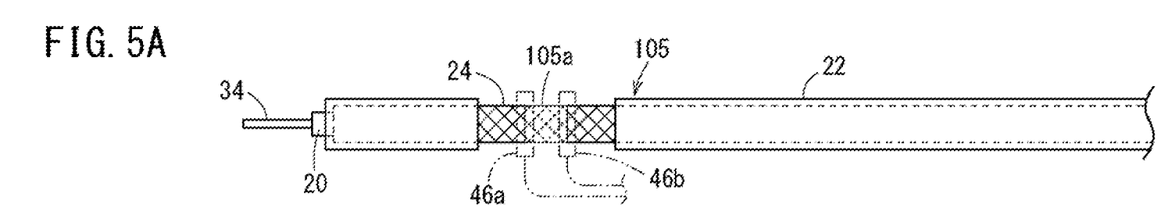
FIG. 5A is a sixth view illustrating the method of manufacturing a catheter following FIG. 4.

The annealing step (Step S6 in FIG. 2) is performed before an elapse of a considerable length of time after the cooling step. In the annealing step, unnecessary residual stress of the reinforcement wire 32 is removed by heating a predetermined axial section (for example, axial central portion) of the reinforcement body 24 which is exposed to the end portion-forming portion 104a. Specifically, as illustrated in FIG. 5A, the predetermined section is heated by an electric power load generated by respectively attaching a pair of electrode plugs 46a and 46b to one end and the other end of the predetermined section and energizing the pair of electrode plug 46a and 46b. Since large current is applied to the reinforcement wire 32 in the predetermined section, the temperature of the reinforcement wire 32 increases in an instant and the reinforcement wire 32 is annealed. As a result, the annealing step is finished in a short period of time (for example, 0.1 seconds or shorter).

During the annealing step, heat is also transferred to the inner layer 20 of the end portion-forming portion 104a, and as described above, the thermal conductivity of the material of the inner layer 20 is considerably lower than that of the reinforcement body 24. For this reason, in a state where the temperature of the inner layer 20 of the end portion-forming portion 104a has decreased, it is possible to strengthen the reinforcement wire 32 by increasing the temperature of only the reinforcement wire 32 having a high thermal conductivity while preventing an extreme increase in the temperature of the inner layer 20. In other words, according to the manufacturing method of the exemplary embodiment, it is possible to anneal only the reinforcement body 24 without melting the inner layer 20 of the end portion-forming portion 104a by performing the cooling step prior to performing the annealing step. As a result, a fifth molded object 105 is molded, and includes an annealed spot (hereinafter, an annealed portion 105a) in the predetermined section of the end portion-forming portion 104a of the fourth molded object 104.

Subsequently, a cutting step is performed on the fifth molded object 105 (Step S7 in FIG. 2). In the cutting step, the reinforcement body 24 at a predetermined position (for example, axial central portion) on the annealed portion 105a, that is, the reinforcement wire 32 is cut via cutting means (not illustrated). Since the residual stress of the reinforcement wire 32 of the annealed portion 105a is removed by annealing, it is possible to prevent motion such as the jumping of a cut end portion of the reinforcement wire 32 being caused by cutting.

Figure 5B:
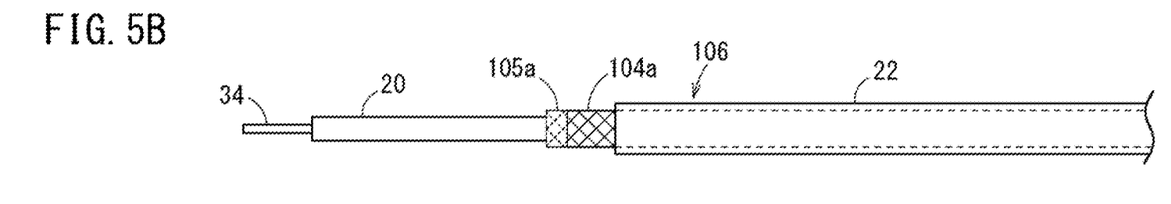
FIG. 5B is a seventh view illustrating the method of manufacturing a catheter following FIG. 5A.

In the cutting step, a device (for example, a fusion cutting device or a cutting device which has the function of annularly cutting an object), which performs cutting while preventing the occurrence of damage to the inner layer 20, may be used as the cutting means. As a result, as illustrated in FIG. 5B, a sixth molded object 106 is formed in which the inner layer 20 remains and a distal side of the reinforcement body 24 is separated and removed from a proximal side of the reinforcement body 24. The cutting means for cutting the reinforcement wire 32 is not limited to specific cutting means and various types of devices using heating, gas, laser beams, ultrasounds, plasmas, and the like may be used.

Subsequently, a distal portion forming step is performed on the sixth molded object 106 (Step S8 in FIG. 2). In the distal portion forming step, the soft tip portion 26 of the tube shaped main body 12 and the distal extension portion 30 of the outer layer 22 are formed in a portion of the sixth molded object 106, to which the reinforcement wire 32 and the inner layer 20 are exposed. The soft tip portion 26 and the distal extension portion 30 may be formed at the same time as in the manufacturing method, or may be formed sequentially in separate operations.

Figure 5C:
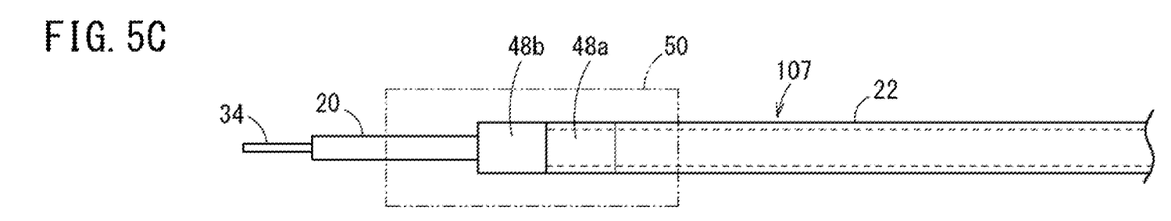
FIG. 5C is an eighth view illustrating the method of manufacturing a catheter following FIG. 5B.

Specifically, the soft tip portion 26 and the distal extension portion 30 are formed at the same time using a heat-shrinkable tube. In this case, as illustrated in FIG. 5C, cylindrical members 48a and 48b, which are formed of the resin of the soft tip portion 26 and the distal extension portion 30 which are stacked, are prepared. The cylindrical member 48a of the distal extension portion 30 is disposed to overlap the reinforcement body 24, and the cylindrical member 48b of the soft tip portion 26 is disposed closer to the distal side than the cylindrical member 48a. The cylindrical member 48b of the soft tip portion 26, which is longer than a finished article in the axial direction, may be used.

A heat-shrinkable tube 50 is shrunk by disposing the heat-shrinkable tube 50 on the outside of the cylindrical members 48a and 48b and heating the heat-shrinkable tube 50. As a result, a seventh molded object 107 is formed in which the cylindrical members 48a and 48b disposed on the inside of the heat-shrinkable tube 50 are shrunk inward in the radial direction, the outer peripheral surfaces of the inner layer 20 and the reinforcement body 24 are coated with the cylindrical members 48a and 48b, and the outer diameter of the soft tip portion 26 and the distal extension portion 30 is substantially the same as the outer diameter of the main extension portion 28. A method of coating the sixth molded object 106 with the soft tip portion 26 and the distal extension portion 30 is not limited to molding using a heat-shrinkable tube. For example, an outer peripheral surface of a distal side of the sixth molded object 106 may be coated with the soft tip portion 26 and the distal extension portion 30 by dipping the distal side of the sixth molded object 106 into molten resin.

Figure 5D:
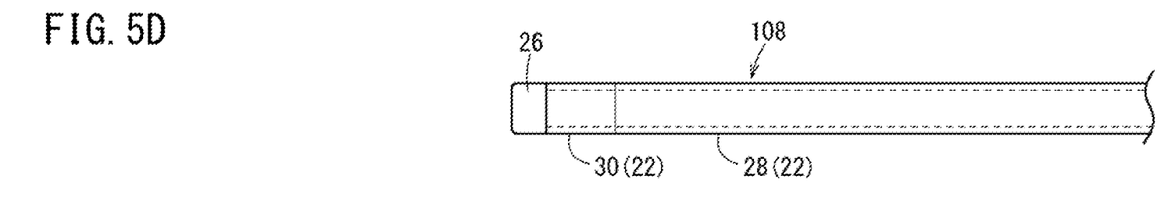
FIG. 5D is a ninth view illustrating the method of manufacturing a catheter following FIG. 5C.

After the seventh molded object 107 is molded, as illustrated in FIG. 5D, the core 34 is taken out from the seventh molded object 107, and the seventh molded object 107 is cut at a predetermined position on the soft tip portion 26 in the axial direction. An eighth molded object 108, in which a distal portion of the tube shaped main body 12 is formed, is formed by rounding a distal edge portion of the soft tip portion 26.

Finally, a hub forming step is performed on the eighth molded object 108 (Step S9 in FIG. 2). In the hub forming step, the protector 14 is mounted on a proximal side of the eighth molded object 108. In a case where the distal portion of the tube shaped main body 12 is to be curved or bent, a shaping process is suitably performed. The catheter 10 illustrated in FIG. 1 is manufactured by firmly fixing the hub 16, which is molded separately, to a proximal portion of the eighth molded object 108, and attaching the hub 16 to a proximal portion of the protector 14.

As described above, according to the method of manufacturing the catheter 10 of the exemplary embodiment, when the annealing step is performed, it is possible to prevent the melting of the inner layer 20 by performing the cooling step prior to performing the annealing step. That is, even if heat applied to the reinforcement body 24 is transferred to the inner layer 20 during the annealing step, it is possible to decrease the temperature of the inner layer 20 by performing the cooling step, and thus it is possible to prevent the temperature from increasing to the melting point. As a result, it is possible to maintain the molding state of the inner layer 20 of the catheter 10 well, and to manufacture the catheters 10 at a high yield.

In this case, since the inner layer 20 is formed of thermoplastic resin, it is possible to easily mold the catheter 10 at low cost. Since it is possible to prevent the melting of thermoplastic resin having a low melting point by performing the cooling step, it is possible to smoothly process the annealing step and processes following the annealing step, and to manufacture the catheter 10 with high accuracy.

Since the temperature of the end portion-forming portion 104*a* of the fourth molded object 104 is cooled to −10° C. or lower in the cooling step, even if high heat is applied to the inner layer 20 during the annealing step, it is possible to more reliably prevent the melting of the inner layer 20. It is possible to considerably shorten the length of time required to perform the cooling step by dipping the end portion-forming portion 104*a* into the liquid nitrogen LN and cooling the end portion-forming portion 104*a*. It is possible to efficiently manufacture the medical elongated body 10.

Since the thermal conductivity of the inner layer 20 is in a range of 0.05 $W·m^{-1}·K^{-1}$ to 1 $W·m^{-1}·K^{-1}$, and the thermal conductivity of the reinforcement body 24 is in a range of 5 $W·m^{-1}·K^{-1}$ to 500 $W·m^{-1}·K^{-1}$, even if the reinforcement body 24 is heated during the annealing step, it is possible to avoid a large amount of heat being transferred to the inner layer 20. As a result, it is possible to satisfactorily anneal only the reinforcement body 24.

The method of manufacturing the catheter 10 is not limited to that in the exemplary embodiment above and naturally, various modification examples or application examples can be adopted. For example, in the cooling step (method of cooling the end portion-forming portion 104*a* of the fourth molded object 104), not only the end portion-forming portion 104*a* may be dipped into the liquid nitrogen LN as described above, but also various methods may be used. Hereinafter, several modification examples of the cooling step will be described.

Figure 6A:
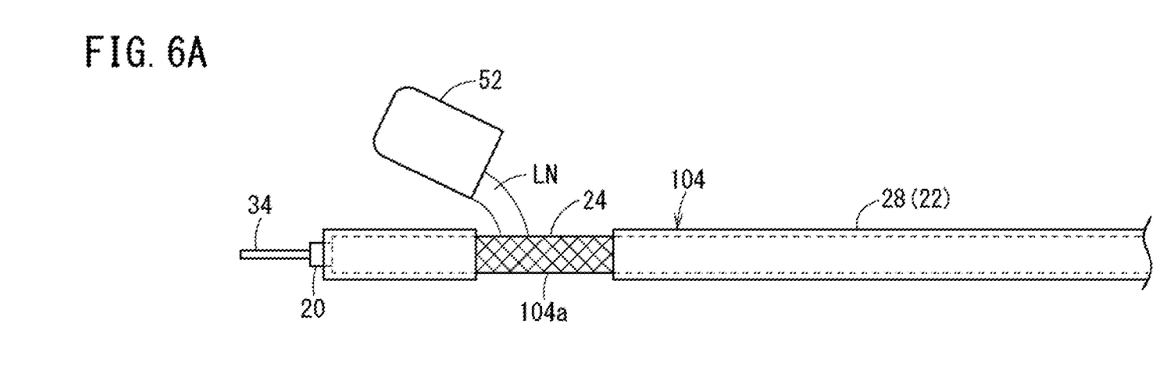
FIG. 6A is a view illustrating a cooling step of a first modification example according to the disclosure.

As illustrated in FIG. 6A, in a cooling step of a first modification example, the liquid nitrogen LN reserved in a container 52 is poured onto the end portion-forming portion 104*a*. Since the liquid nitrogen LN has high cooling performance, it is possible to obtain sufficient effects by dropping a small amount of the liquid nitrogen LN onto the end portion-forming portion 104*a*. As such, in the cooling step, even if the liquid nitrogen LN is poured thereonto, it is possible to decrease the temperature of the inner layer 20 of the end portion-forming portion 104*a*.

Figure 6B:
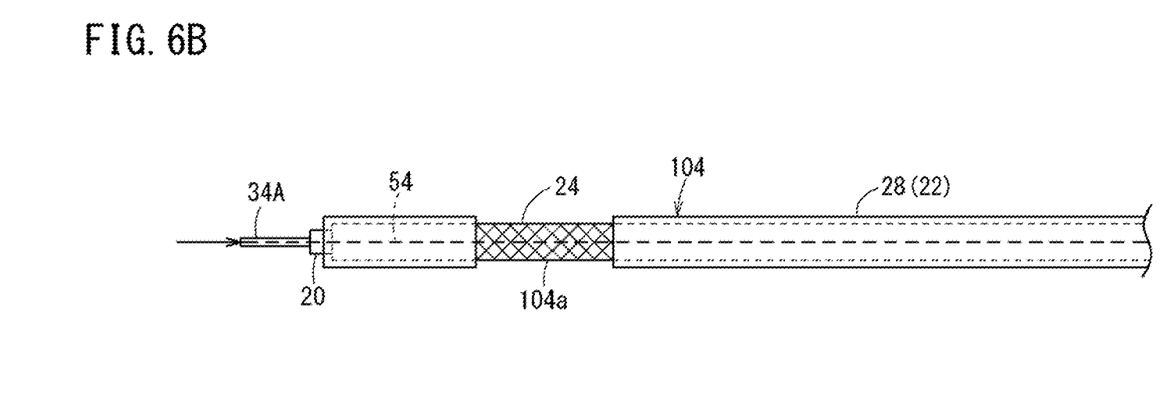
FIG. 6B is a view illustrating a cooling step in a second modification example according to the disclosure.
Figure 7:
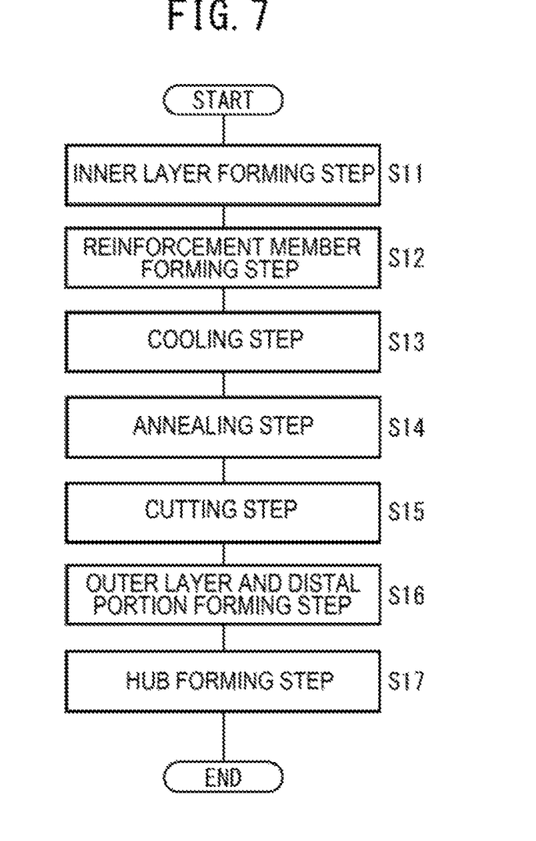
FIG. 7 is a flowchart illustrating a method of manufacturing a catheter of a second exemplary embodiment.

As illustrated in FIG. 6B, in a cooling step of a second modification example, a core 34A coated with the inner layer 20 is formed of a hollow tube shaped member in advance, and a flow path 54 for a coolant is provided in an axial central portion of the core 34A. The inner layer 20 of the end portion-forming portion 104*a* is cooled from the inside by allowing the coolant to flow through the flow path 54. Naturally, the liquid nitrogen LN may be selected as a coolant, and a coolant may be suitably selected from cooling fluids (including water) and cooling gases (including air) according to a heating temperature of the annealing step.

In a case where a coolant is allowed to flow through the flow path 54 of the core 34A in the cooling step, preferably, the inner layer 20 is continuously cooled during the annealing step as well. That is, in this manufacturing method, it is important to decrease the temperature of the inner layer to a temperature at which the inner layer 20 is not to be melted in the annealing step. It is also possible to satisfactorily prevent the melting of the inner layer 20 in a case where the inner layer 20 is cooled from the inside of the fourth molded object 104 as in the second modification example. In a case where an inner layer 20 side is cooled, a solid core (not illustrated) formed of a material having a high thermal conductivity may be used, and a distal side of the inner layer 20 may be cooled by cooling the core exposed on a distal side of the fourth molded object 104, and transferring a cooling temperature to the distal side of the inner layer 20 along the core.

In another modification example of the cooling step, the end portion-forming portion 104*a* may be cooled by a dedicated cooling device (not illustrated). An example of the cooling device is an air cooler (spot cooling device) that cools and injects air. If the air cooler is used, it is possible to simply set a cooling temperature to −10° C. or lower. Alternatively, a Peltier element may be brought into contact with the end portion-forming portion 104*a*, and a contact portion therebetween may be cooled by supplying electric power to the Peltier element. In a case where such a cooling device is used, as in the second modification example, the cooling device may cool the inner layer 20 from the inside of the inner layer 20 (core 34A side) in addition to cooling the inner layer 20 from the outside of the inner layer 20.

In the cooling step, the end portion-forming portion 104*a* may be cooled by storing the fourth molded object 104 in a cold chamber prior to performing the annealing step or during the annealing step. That is, even if the fourth molded object 104 is stored in a low-temperature place such that the fourth molded object 104 is gradually cooled, it is possible to decrease the temperature of the inner layer 20 to a temperature at which the melting of the inner layer 20 does not occur during the annealing step.

Hereinafter, a method of manufacturing the catheter 10 according to a second exemplary embodiment of the disclosure will be described with reference to FIGS. 7 to 9D. Note that in the following description, the same reference signs will be assigned to the same configuration elements or configuration elements having the same functions as those in the method of manufacturing the catheter 10 of the first exemplary embodiment, and detailed description thereof will be omitted.

The method of manufacturing the catheter 10 of the second exemplary embodiment is different from the method of manufacturing the catheter 10 of the first exemplary embodiment in that a cooling step, a annealing step, and a cutting step (Steps S13, S14, and S15 in FIG. 7) are performed before the outer layer 22 is formed. Note that the same processes as those in the inner layer forming step, the reinforcement body forming step, and the hub forming step of the first exemplary embodiment are performed in an inner layer forming step, a reinforcement body forming step, and a hub forming step (Steps S11, S12, and S17 in FIG. 7).

Figure 8:
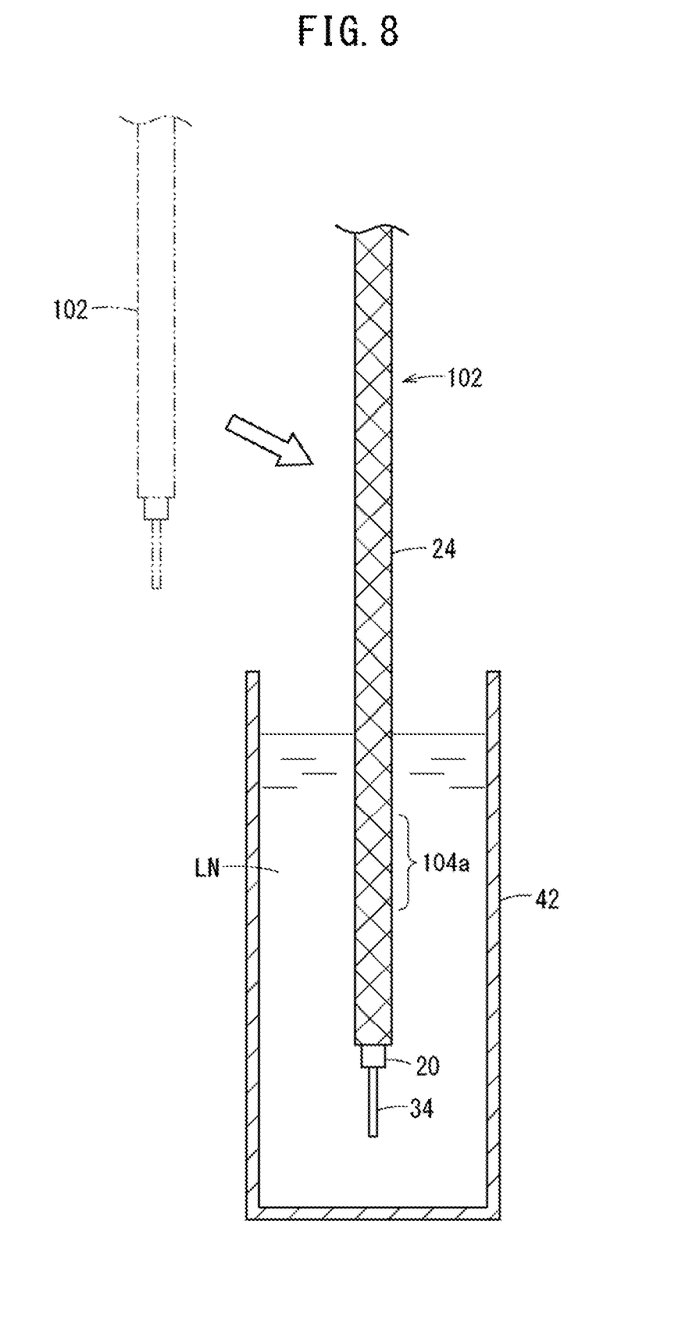
FIG. 8 is a first view illustrating the method of manufacturing a catheter of the second exemplary embodiment.

Specifically, as illustrated in FIG. 8, in the cooling step (Step S13 in FIG. 7), the second molded object 102 is dipped into the liquid nitrogen LN reserved in the reservoir 42. The second molded object 102 is structured via the inner layer forming step (Step S11 in FIG. 7) and the reinforcement body forming step (Step S12 in FIG. 7) such that an outer periphery of the core 34 is covered with the inner layer 20 and the reinforcement body 24. In this case, the dipping depth of a distal side of the second molded object 102 is set such that the end portion-forming portion 104*a*, which is set in a predetermined range of the second molded object 102 in the axial direction, is dipped into the liquid nitrogen LN.

Figure 9A:
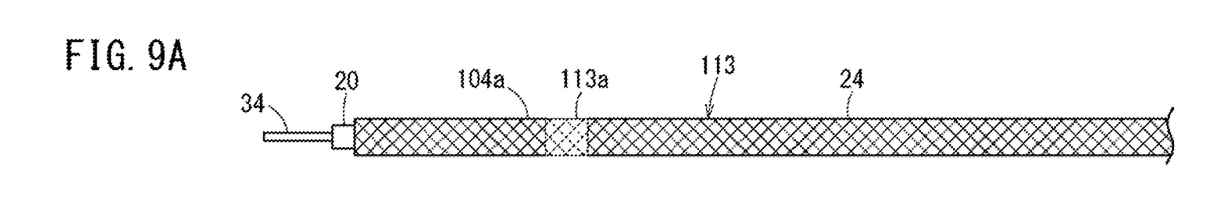
FIG. 9A is a second view illustrating the method of manufacturing a catheter following FIG. 8.

In the annealing step (Step S14 in FIG. 7), a predetermined portion or a spot of the second molded object 102, which is cooled by the liquid nitrogen LN, is annealed. As a result, as illustrated in FIG. 9A, a third molded object 113 is formed in which the reinforcement body 24 includes an annealed portion 113*a*. In the annealing step, the melting of the inner layer 20, the temperature of which is decreased by the cooling step, is avoided, and the molding state of the inner layer 20 is maintained.

Figure 9B:
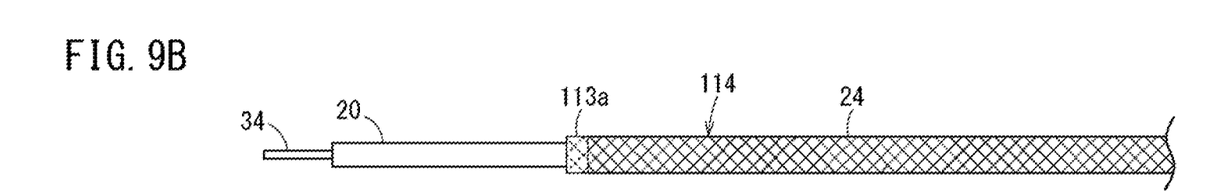
FIG. 9B is a third view illustrating the method of manufacturing a catheter following FIG. 9A.

In the cutting step (Step S15 in FIG. 7), the annealed portion 113*a* of the third molded object 113 is cut by arbitrary cutting means (a fusion cutting device, a cutting device, or the like). As a result, as illustrated in FIG. 9B, a fourth molded object 114 is formed in which the distal side of the reinforcement body 24 is removed (separated). Since residual stress of the annealed portion 113*a* is removed by annealing, the annealed portion 113*a* is cut while the jumping of the annealed portion is prevented during cutting.

Figure 9C:
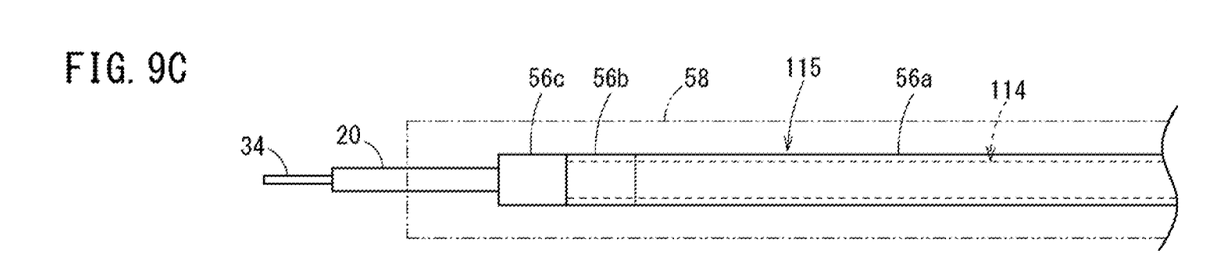
FIG. 9C is a fourth view illustrating the method of manufacturing a catheter following FIG. 9B.

In the manufacturing method of the second exemplary embodiment, an outer layer and distal portion forming step (Step S16 in FIG. 7) is performed after the cutting step. As illustrated in FIG. 9C, in the outer layer and distal portion forming step, cylindrical members 56*a*, 56*b*, and 56*c*, which are respectively made of resins of the main extension portion 28, the distal extension portion 30, and the soft tip portion 26 of the catheter 10, are disposed on the outside of the fourth molded object 114 in the radial direction. A heat-shrinkable tube 58 longer than the tube shaped main body 12 is disposed on the outside thereof. The cylindrical member 56*b* of the distal extension portion 30 is positioned on the annealed portion 113*a*.

The long heat-shrinkable tube 58 is shrunk by heating, and thus, the main extension portion 28, the distal extension portion 30, and the soft tip portion 26 are firmly fixed to an outer peripheral surface of the fourth molded object 114. Note that the main extension portion 28, the distal extension portion 30, and the soft tip portion 26 may be formed individually. Even if the outer layer and distal portion forming step is performed after the cutting step, it is possible to form a fifth molded object 115 in which the outer layer 22 is formed with high accuracy.

Figure 9D:
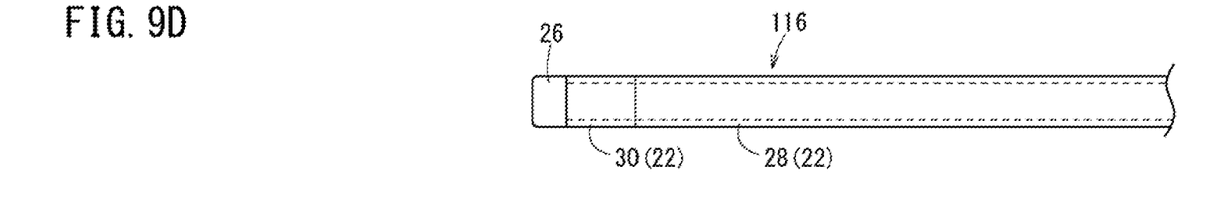
FIG. 9D is a fifth view illustrating the method of manufacturing a catheter following FIG. 9C.

As illustrated in FIG. 9D, a sixth molded object 116 is obtained by detaching the core 34 from the fifth molded object 115, and cutting the soft tip portion 26 of the fifth molded object 115. The catheter 10 illustrated in FIG. 1 is manufactured by attaching the protector 14 and the hub 16 to a proximal side of the sixth molded object 116 via the hub forming step (Step S17 in FIG. 7).

As such, in the method of manufacturing the catheter 10 of the second exemplary embodiment, even if the reinforcement body 24 is heated, it is possible to prevent the melting of the inner layer 20 by performing the cooling step prior to performing the annealing step. It is possible to reduce the amount of a material used in the formation of the outer layer 22 by forming the outer layer 22 after cutting the reinforcement body 24, and it is possible to reduce the cost.

The detailed description above describes a method of manufacturing a medical elongated body. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of manufacturing a medical elongated body including an inner layer, an outer layer covering the outside of the inner layer, and a reinforcement body provided between the inner layer and the outer layer, the method comprising:
    an inner layer forming step of forming the inner layer;
    a reinforcement body forming step of forming the reinforcement body on an outer peripheral surface of the inner layer immediately after the inner layer forming step;
    after forming the reinforcement body on the outer peripheral surface of the inner layer, a cooling step of cooling at least a predetermined spot of the inner layer; and
    an annealing step of annealing the reinforcement body which overlaps the predetermined spot of the inner layer cooled by the cooling step;
    wherein in the cooling step, the predetermined spot is cooled by a coolant having a temperature of −10° C. or lower; and
    wherein in the cooling step, the predetermined spot is cooled by dipping the predetermined spot in liquid nitrogen before performing the annealing step.

2. The method of manufacturing the medical elongated body according to claim 1, wherein the inner layer is formed of thermoplastic resin.

3. The method of manufacturing the medical elongated body according to claim 1, wherein the inner layer is formed of resin having a thermal conductivity in a range of 0.05 $W \cdot m^{-1} \cdot K^{-1}$ to 1 $W \cdot m^{-1} \cdot K^{-1}$, and the reinforcement body is formed of a reinforcement wire having a thermal conductivity in a range of 5 $W \cdot m^{-1} K^{-1}$ to 500 $W \cdot m^{-1} \cdot K^{-1}$.

4. The method of manufacturing the medical elongated body according to claim 1, further comprising an outer layer forming step of forming the outer layer such that the reinforcement body on the outer peripheral surface of the inner layer is covered by the outer layer.

5. The method of manufacturing the medical elongated body according to claim 4, wherein the outer layer forming step is performed after the cooling and annealing steps.

6. A method of manufacturing a medical elongated body including an inner layer, an outer layer covering the outside of the inner layer, and a reinforcement body provided between the inner layer and the outer layer, the method comprising:
    an inner layer forming step of forming the inner layer;
    a reinforcement body forming step of forming the reinforcement body on an outer peripheral surface of the inner layer immediately after the inner layer forming step;
    after forming the reinforcement body on the outer peripheral surface of the inner layer, a cooling step of cooling at least a predetermined spot of the inner layer;
    an annealing step of annealing the reinforcement body which overlaps the predetermined spot of the inner layer cooled by the cooling step; and
    further comprising an outer layer forming step of forming the outer layer such that the reinforcement body on the outer peripheral surface of the inner layer is covered by the outer layer;
    wherein the outer layer forming step is performed before the cooling and annealing steps, and further comprising, an outer layer removing step of removing a portion of the outer layer and thereby defining the predetermined spot of the inner layer.

7. A method of manufacturing a medical elongated body, the method comprising:
forming an inner layer;
forming a reinforcement body on an outer peripheral surface of the inner layer;
cooling at least a predetermined portion of the inner layer; and
after cooling, annealing at least the reinforcement body which overlaps the predetermined portion of the inner layer;
wherein in the cooling step, the predetermined portion is cooled by dipping at least the predetermined portion in a coolant before performing the annealing step.

8. The method of manufacturing the medical elongated body according to claim 7, wherein the inner layer is formed of a resin and the reinforcement body is formed of a reinforcement wire, the reinforcement body having a higher thermal conductivity than the inner layer.

9. The method of manufacturing the medical elongated body according to claim 8, wherein the resin has a thermal conductivity in a range of 0.05 $W \cdot m^{-1} \cdot K^{-1}$ to 1 $W \cdot m^{-1} \cdot K^{-1}$ and the reinforcement body has a thermal conductivity in a range of 5 $W \cdot m^{-1} \cdot K^{-1}$ to 500 $W \cdot m^{-1} \cdot K^{-1}$.

10. The method of manufacturing the medical elongated body according to claim 7, further comprising forming an outer layer such that the reinforcement body on the outer peripheral surface of the inner layer is covered by the outer layer.

11. The method of manufacturing the medical elongated body according to claim 10, wherein the outer layer forming step is performed before the cooling and annealing steps.

12. The method of manufacturing the medical elongated body according to claim 11, further comprising an outer layer removing step of removing a portion of the outer layer and thereby defining the predetermined portion of the inner layer.

13. The method of manufacturing the medical elongated body according to claim 10, wherein the outer layer forming step is performed after the cooling and annealing steps.

14. The method of manufacturing the medical elongated body according to claim 7, wherein in the cooling step, the predetermined portion is cooled by a coolant having a temperature of −10° C. or lower.

15. A method of manufacturing a medical elongated body including an inner layer, an outer layer covering the outside of the inner layer, and a reinforcement body provided between the inner layer and the outer layer, the method comprising:
an inner layer forming step of forming the inner layer;
a reinforcement body forming step of forming the reinforcement body on an outer peripheral surface of the inner layer immediately after the inner layer forming step;
after forming the reinforcement body on the outer peripheral surface of the inner layer, a cooling step of cooling at least a predetermined spot of the inner layer; and
an annealing step of annealing the reinforcement body which overlaps the predetermined spot of the inner layer cooled by the cooling step;
wherein in the cooling step, the predetermined spot is cooled by dipping the predetermined spot in coolant before performing the annealing step.

* * * * *